(12) United States Patent
Masini et al.

(10) Patent No.: US 9,387,084 B2
(45) Date of Patent: Jul. 12, 2016

(54) ANTERIOR STABILIZED PCL RETAINING TOTAL KNEE PROSTHESIS

(71) Applicant: Howmedica Osteonics Corp., Mahwah, NJ (US)

(72) Inventors: Michael Masini, Ann Arbor, MI (US); Evan Leibowitz, Linden, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/204,016

(22) Filed: Mar. 11, 2014

(65) Prior Publication Data

US 2014/0257502 A1 Sep. 11, 2014

Related U.S. Application Data (60) Provisional application No. 61/775,902, filed on Mar. 11, 2013.

(51) Int. Cl.
*A61F 2/38* (2006.01)
*A61F 2/30* (2006.01)

(52) U.S. Cl.
CPC ..... *A61F 2/3886* (2013.01); *A61F 2002/30688* (2013.01); *A61F 2002/30772* (2013.01); *A61F 2002/30878* (2013.01)

(58) Field of Classification Search
CPC ....... A61F 2/38; A61F 2/3859; A61F 2/3868; A61F 2/3886; A61F 2/389
USPC .......... 623/20.14–20.17, 20.21, 20.24–20.29, 623/20.31–20.36
See application file for complete search history.

(56) References Cited

U.S. PATENT DOCUMENTS

| | | | |
|---|---|---|---|
| 6,325,828 B1 | 12/2001 | Dennis et al. | |
| 6,962,607 B2 * | 11/2005 | Gundlapalli | A61F 2/30942 623/22.29 |
| 2009/0210066 A1 | 8/2009 | Jasty | |
| 2010/0016977 A1 | 1/2010 | Masini | |
| 2012/0095563 A1 * | 4/2012 | Sanford et al. | 623/20.27 |

OTHER PUBLICATIONS

Smith & Nephew Journey, "Design Rationale: Bi-Cruciate Stabilized Knee System", © 2006.

* cited by examiner

*Primary Examiner* — Marcia Watkins
(74) *Attorney, Agent, or Firm* — Lerner, David, Littenberg, Krumholz & Mentlik, LLP (57) ABSTRACT

A knee prosthesis that includes a tibial component and femoral component. The tibial component includes an articular surface, a posterior portion and an anterior portion. The posterior portion includes a recess for receipt of a posterior cruciate ligament. The anterior portion includes a post extending therefrom. The post includes a posterior surface. The femoral component includes a condylar portion and an intercondylar portion. The intercondylar portion includes a posterior recess for receipt of the posterior cruciate ligament, a cam, and an engagement recess for receipt of the post. The cam includes a sliding surface and is disposed between the engagement recess and posterior recess. The sliding surface of the cam slides along the posterior surface of the post for restricting anterior subluxation of a femur bone when the articular surface and the condylar portion articulates through flexion of a knee joint.

14 Claims, 8 Drawing Sheets

ANTERIOR STABILIZED PCL RETAINING TOTAL KNEE PROSTHESIS

CROSS-REFERENCE TO RELATED APPLICATIONS

The present application claims the benefit of the filing date of U.S. Provisional Patent Application No. 61/775,902 filed on Mar. 11, 2013, the disclosure of which is hereby incorporated herein by reference.

BACKGROUND OF THE INVENTION

The present invention relates generally to total knee arthroplasty ("TKA"). More specifically, this invention relates to an anterior stabilized posterior cruciate ligament ("PCL") retaining total knee replacement prosthesis.

During articulation of a natural knee joint, flexion between the tibia and the femur takes place about a transverse axis while some relative rotation between the tibia and femur occurs about a longitudinal axis. Such flexion and rotation is necessary to carry out a normal gate cycle. Rotational stability of the natural knee is provided by the collateral and cruciate ligaments. Specifically, the anterior cruciate ligament ("ACL") and PCL resist paradoxical movement in which the femur and tibia translate relative to each other in the posterior-anterior direction, while the collateral ligaments provide transverse stability of the knee joint. Further, all of these ligaments contribute to proprioception. When the natural knee joint is replaced by a total knee prosthesis, frequently either the ACL or both the ACL and PCL are removed.

A TKA that retains the PCL and removes the ACL, often called cruciate-retaining TKA, traditionally sacrifices the ACL such that the knee behaves as an ACL-deficient knee. This behavior may result in paradoxical movement during certain activities, such as physical activities utilizing a heel strike. Such paradoxical movement results in translation of the femur anteriorly with respect to the tibia until the collateral ligaments are tensioned to prevent further anterior motion.

A TKA that removes both the ACL and PCL and substitutes for the PCL is commonly known as posterior stabilized TKA. The most common form of PCL substitution is achieved by using a cam and post mechanism to substitute for PCL removal while, once again, characteristically sacrificing the ACL. Such devices primarily focus on the substitution of the PCL and consequently have characteristics of an ACL deficient knee such as anterior subluxation of the tibia in extension. Further, the removal of the PCL reduces proprioception, which may affect a patient's balance post-procedure.

Most recently, devices designated as "bicruciate substituting" have been designed, where both the ACL and PCL are removed and substituted. Certain of these devices utilize a post and cam mechanism to substitute for both the ACL and PCL. However, the removal and substitution of both cruciate ligaments reduces proprioception and natural knee function, particularly for the active individual. Further, the cam and post must remain engaged throughout flexion and extension, which may increase the likelihood of failure and wear.

Thus, currently available devices may sacrifice but not substitute for the ACL and may remove both cruciate ligaments limiting post-procedure proprioception. However, the ACL is an important ligamentous constraint for joint stability, and proprioception is important for balance particularly in more vigorous activities that require quicker response time. The result has been implants which generally function insufficiently for high levels of activity due to paradoxical movement and limited proprioception.

Therefore, there is a need for a total knee prosthesis that retains the PCL and provides the anterior stability necessary to support normal kinematics, improved proprioception, and that has reproducible and favorable long term results, particularly for the active patient.

BRIEF SUMMARY OF THE INVENTION

According to one embodiment of the present invention, a knee prosthesis that includes a tibial component and femoral component is disclosed herein. The tibial component includes an articular surface, a posterior portion and an anterior portion. The posterior portion includes a recess for receipt of a posterior cruciate ligament. The anterior portion includes a post extending therefrom. The post includes a posterior surface. The femoral component includes a condylar portion and an intercondylar portion. The intercondylar portion includes a posterior recess for receipt of the posterior cruciate ligament, a cam, and an engagement recess for receipt of the post. The cam includes a sliding surface and is disposed between the engagement recess and posterior recess. The sliding surface of the cam slides along the posterior surface of the post for restricting anterior subluxation of a femur bone when the articular surface and the condylar portion articulates through flexion of a knee joint.

Further, the sliding surface of the cam may slide along the posterior surface of the post when the articular surface and the condylar portion articulate from 0 to 40 degrees of flexion of the knee joint. Additionally, the sliding surface of the cam may not contact the posterior surface of the post when the articular surface and the condylar portion articulate beyond 40 degrees of flexion of the knee joint.

According to another embodiment of the present invention, a method for implanting a knee prosthesis. The method includes resecting a femur and tibia such that the posterior cruciate ligament is retained. Further included in the method is fixing a tibial component to the resected tibia such that the posterior cruciate ligament passes through a recess of the tibial component. The tibial component includes an articular surface and an anterior portion. The anterior portion includes a post extending therefrom. The post includes a posterior surface. Additionally included in the method is fixing a femoral component to the resected femur such that the posterior cruciate ligament passes through a posterior recess of the femoral component. The femoral component includes a condylar portion and an intercondylar portion. The intercondylar portion includes a cam and an engagement recess for receipt of the post. The cam includes a sliding surface and is disposed between the engagement recess and posterior recess. The sliding surface of the cam slides along the posterior surface of the post for restricting anterior subluxation of a femur when the articular surface and the condylar portion articulate through flexion of a knee joint.

BRIEF DESCRIPTION OF THE DRAWINGS

These and other features, aspects, and advantages of the present invention will become better understood with regard to the following description, appended claims, and accompanying drawings where:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face and the term "posterior" means toward the back of the body. Also, as used herein, the terms "about," "generally" and "substantially" are intended to mean that slight deviations from absolute are included within the scope of the term so modified.

Figure 1A:
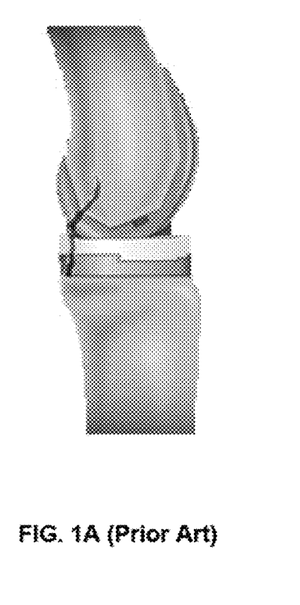
FIGS. 1A and 1B shows an example of the paradoxical movement allowed by prior art total knee prostheses.
Figure 1B:
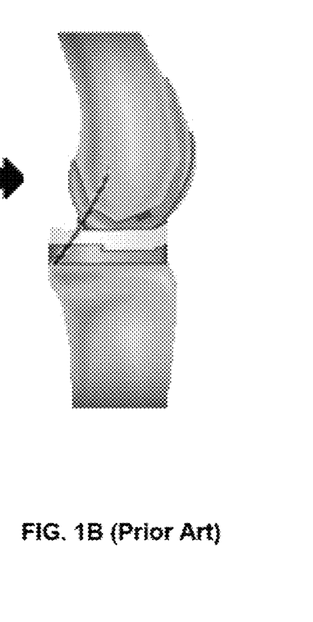

FIGS. 1A and 1B show a prior art device wherein the PCL is retained and the ACL is sacrificed. During certain activities, particularly activities utilizing a heel strike, paradoxical movement may occur in which the femur translates anteriorly, as best shown in FIG. 1B, until the PCL engages to pull the femur back into alignment. Thus, in prior art devices that do not stabilize for the removal of the ACL, the femur may be subluxed anteriorly through approximately 0-40 degrees of flexion.

Figure 2:
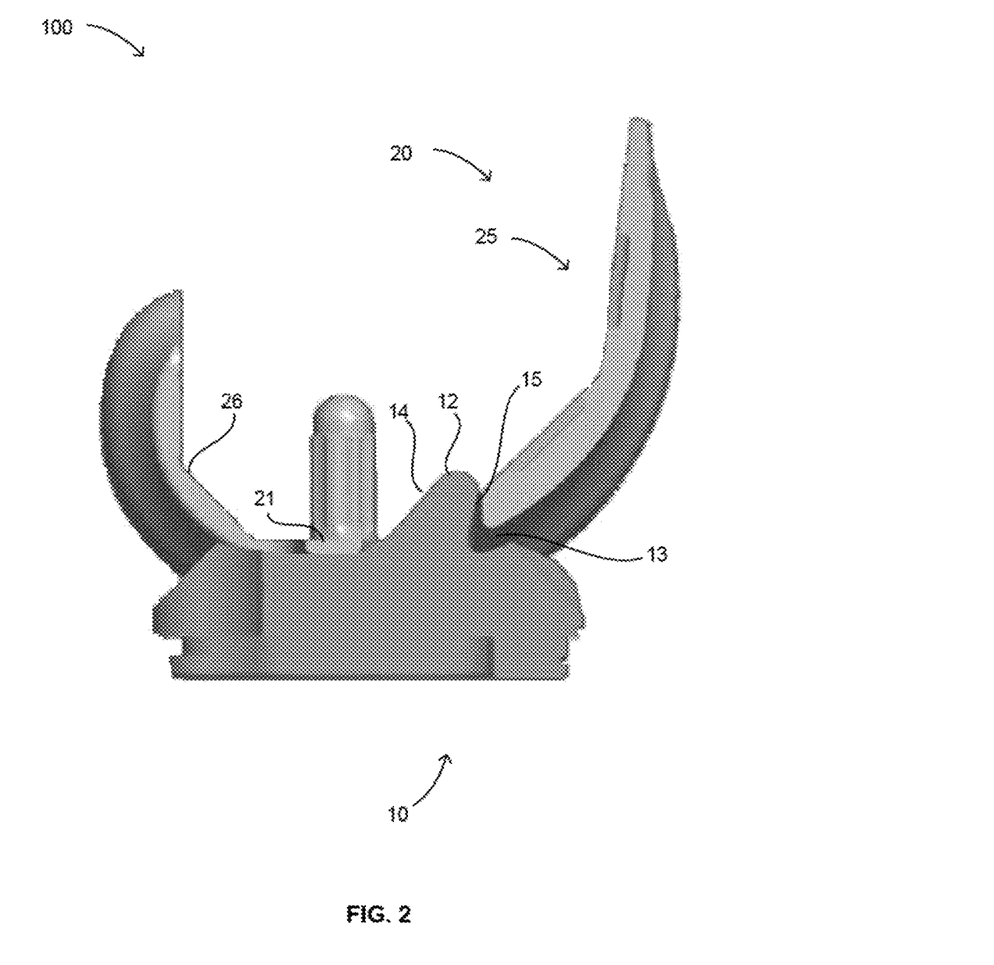
FIG. 2 shows a cross-sectional side view of an embodiment of a total knee prosthesis of the present invention that includes a femoral component and a tibial component.

FIG. 2 depicts an anterior stabilized PCL retaining total knee prosthesis ("TKA prosthesis") 100 in accordance with the present invention. The TKA prosthesis 100 includes a tibial component 10 and a femoral component 20.

Figure 3:
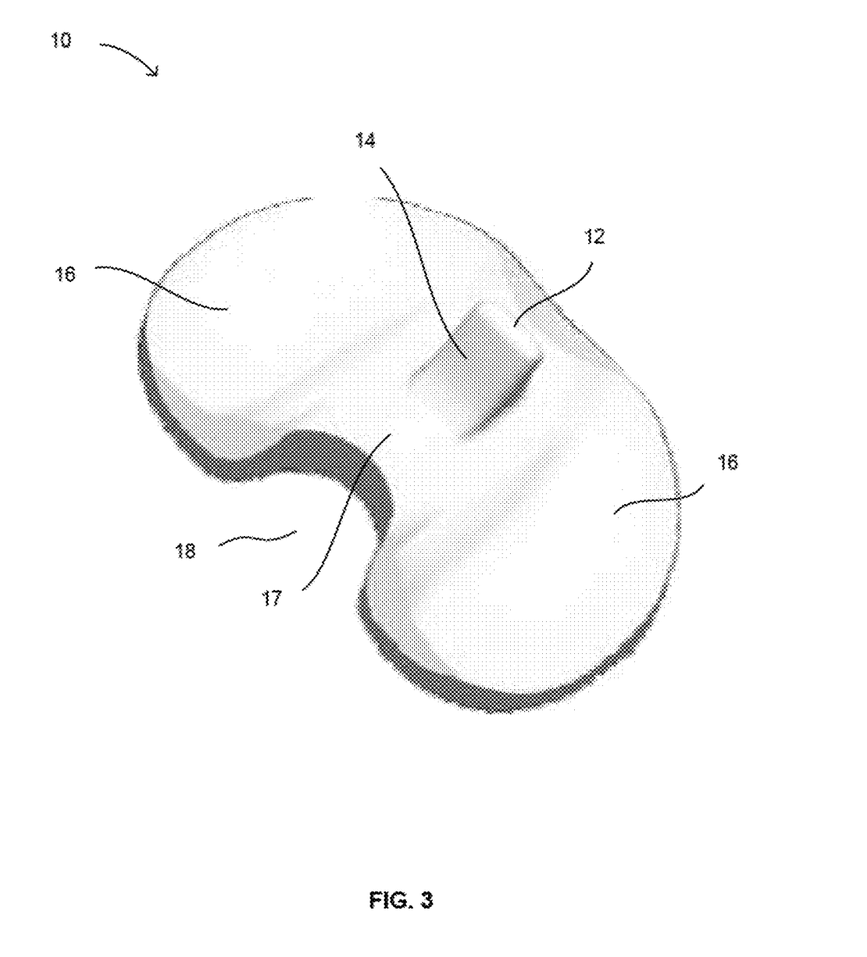
FIG. 3 shows a perspective view of the tibial insert of the total knee prosthesis of FIG. 2.

The tibial component 10, as depicted by FIG. 3, includes articular surfaces 16, a post 12, and a recess 18. The articular surfaces 16 are concave to receive and articulate with a condylar portion 22 of the femoral component 20. The periphery of the tibial component 10 is shaped and sized to be connected to a tibial baseplate. The recess 18 is disposed within a posterior portion of the tibial component 10 to provide a passageway for the natural PCL.

Post 12 extends from an anterior portion of the tibial component 10 between the articular surfaces 16. As best shown in FIGS. 2-3 and 5-8, when viewing post 12 in a sagittal plane, post 12 extends from a superior surface 17 of the tibial component 10 in an anteriorly angled direction, which creates a notch or clearance space 13. The post 12 includes a posterior surface 14 that is curved in the sagittal plane to match, in a knee that has an intact ACL and PCL, the track of a point located on a femur as the femur articulates with a tibia through 0-40 degrees of flexion. The posterior surface 14 connects to the superior surface 17, which is similarly curved to provide a smooth transition for a cam of a femoral component that slides between superior and posterior surfaces 14, 17 (shown in FIGS. 5-8). Such curvature of the posterior and superior surfaces 14, 17 accommodates posterior rollback of the femur, which is facilitated by the retained natural PCL. In other words, the curvature allows natural rollback to occur without interference, rather than forcing rollback to occur as would be the case with a post and cam mechanism of a posterior stabilized TKA as a means for substituting for the performance of a sacrificed PCL. This curvature may be custom specific to match the particular patient, or may be predetermined by matching the patient to a database that catalogues a population with similar characteristics. The post 12 also includes an anterior face 15 that partially defines the clearance space 13 for receipt of a portion of the femoral component 20. The anterior face 15 also has a geometry that substantially matches the track of a second point located on a natural femur during normal joint kinematics and during hyperextension.

Figure 4:
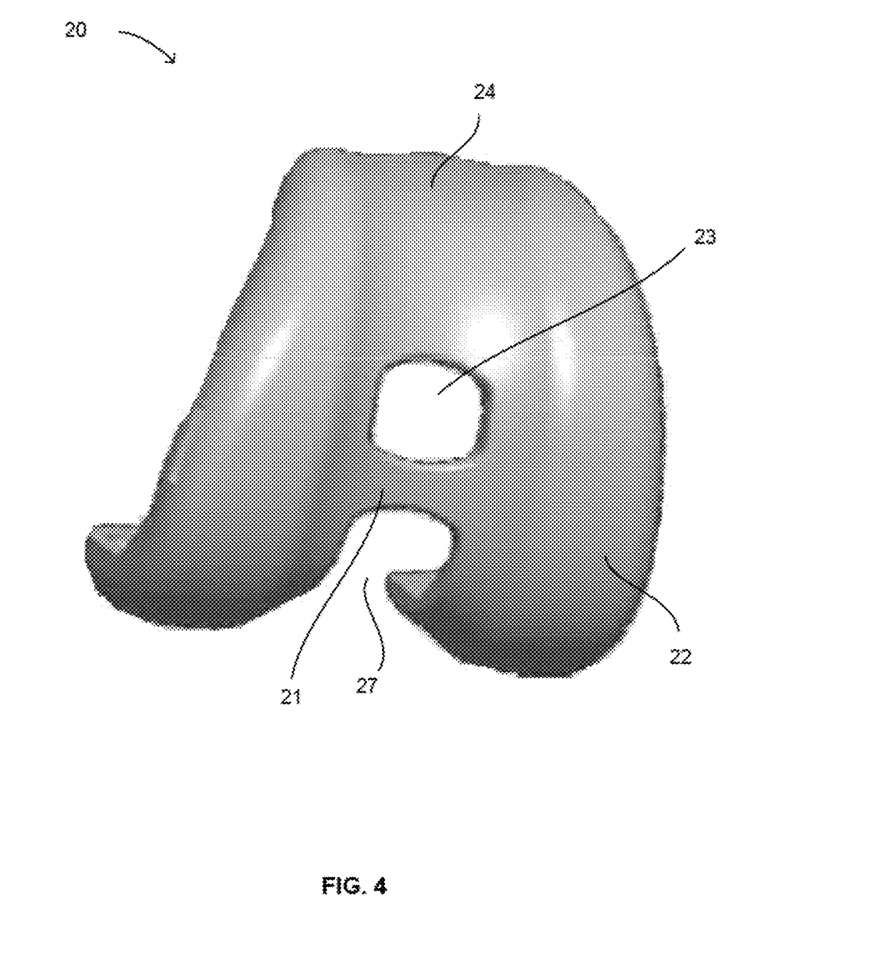
FIG. 4 shows a perspective view of the femoral component of the total knee prosthesis of FIG. 2.

FIG. 4 depicts the femoral component 20, which includes a condylar portion 22 and an intercondylar portion 24. The intercondylar portion 24 includes a posterior recess 27 and an engagement recess 23 extending therethrough, and a cam 21 disposed between the posterior recess 27 and engagement recess 23. The cam 21 includes a sliding surface for sliding along the post 12 of the tibial component 10, particularly along the superior and posterior surfaces 14, 17. The femoral component 20 also includes an abutment surface 29, which is located opposite the cam 21 across the engagement recess 23. The abutment surface 29 is configured to contact the anterior face 15 of the post 12 in instances where the tibia subluxes anteriorly with respect to the femur. While the cam 21 may contact the posterior surface of the post from about 0 to 40 degrees of flexion, the abutment surface 29 is capable of contacting the anterior surface 15 of the post from about 0 to 15 or 20 degrees of flexion.

Figure 5:
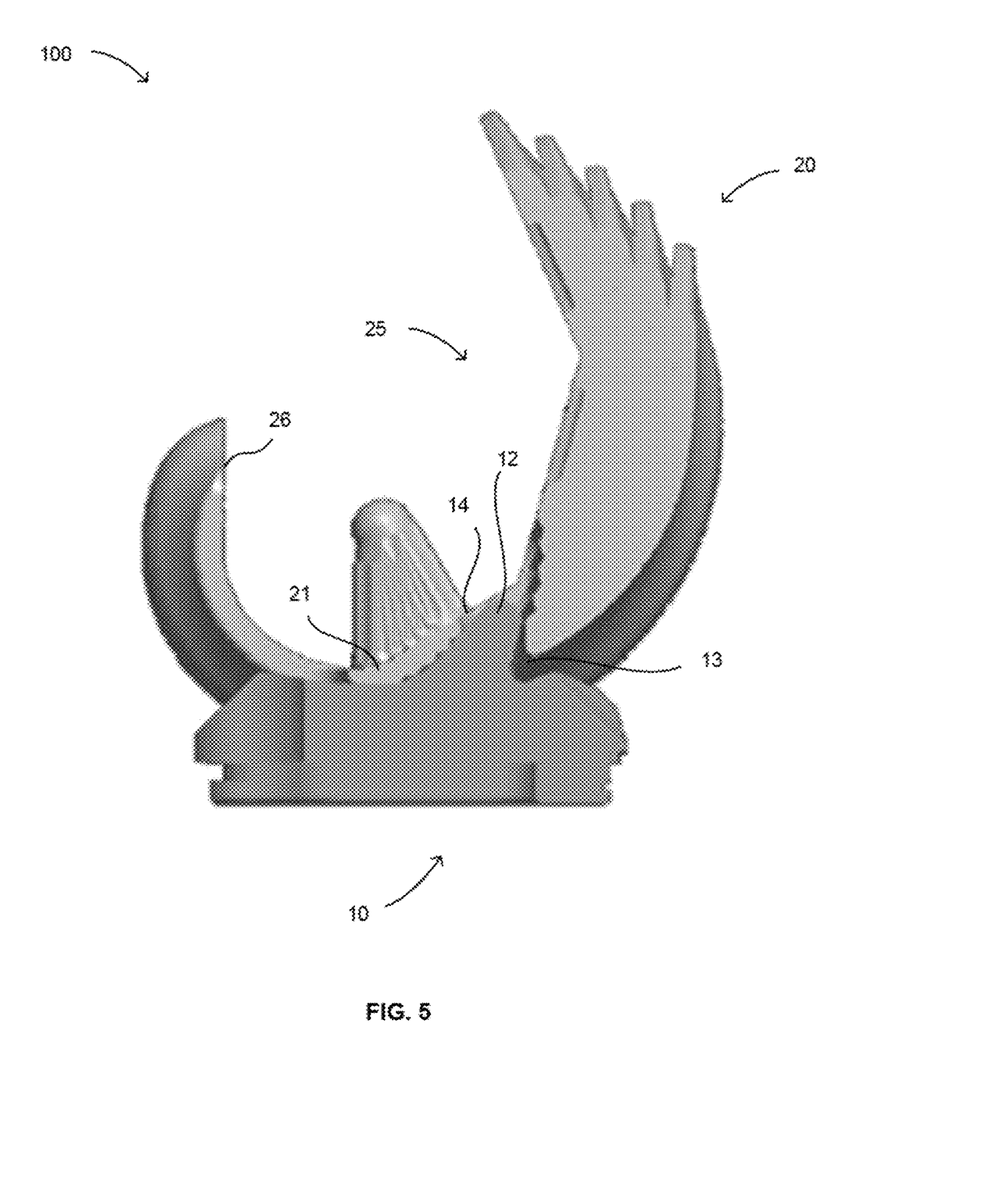
FIG. 5 shows a cross-sectional side view of the total knee prosthesis through 0-30 degrees of flexion.
Figure 6:
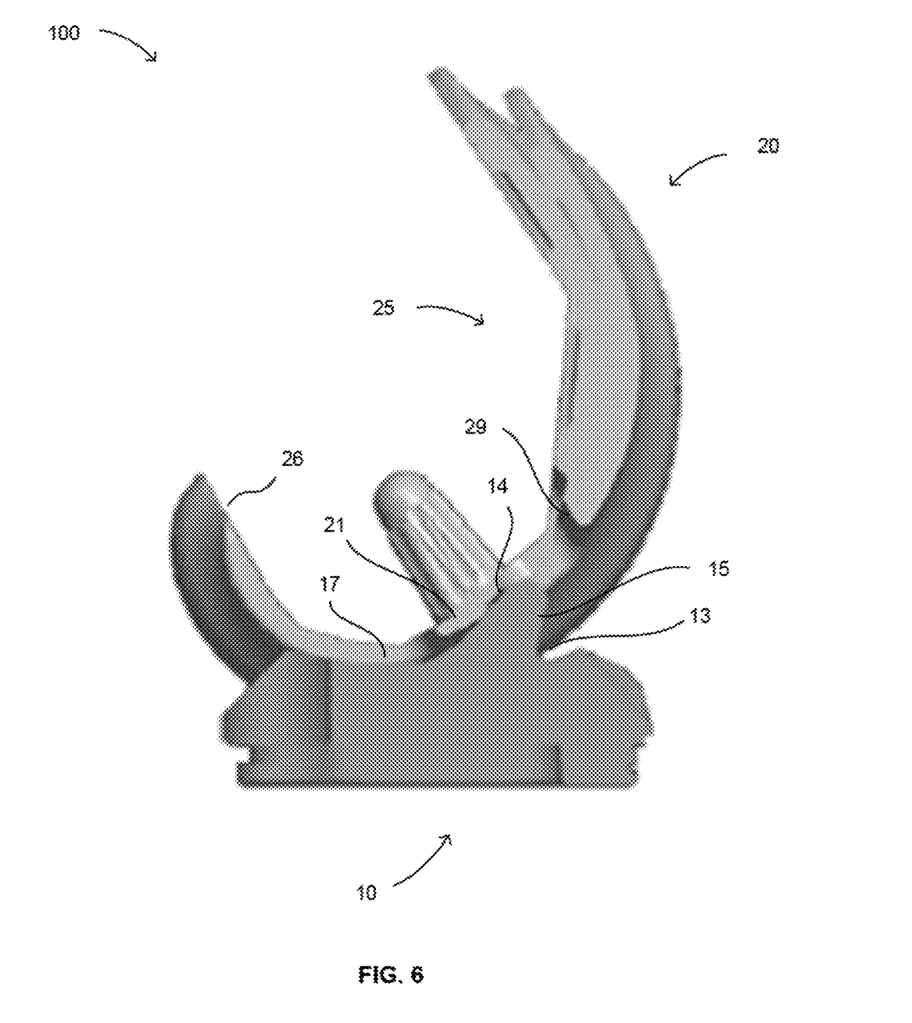
FIG. 6 shows a cross-sectional side view of the total knee prosthesis at 30 and 40 degrees of flexion.

The femoral component 20 further includes a bone contacting surface 25. The bone contacting surface 25 may include a series of planar surfaces 26 that intersect each other at various angles. The number of planar surfaces 26 is dependent on number of resected surfaces of a femur bone. Generally, a femur bone may be resected by five cuts, thus having five resected surfaces. Therefore, the femoral component 20 would have a bone contacting surface 25 including five planar surfaces 26. However, this is merely an example, the bone contacting surface 25 may also include three or four planar surfaces 26 to correspond to a three-cut or four-cut femur bone, respectively FIG. 5 depicts the movement of an implanted TKA prosthesis 100 through flexion of approximately 0 to 30 degrees. FIG. 6 depicts the movement of an implanted TKA prosthesis 100 through shallow flexion of approximately 30 to 40 degrees. Referring to FIGS. 5 and 6, at 0 degrees of flexion, the cam 21 contacts the post 12 at the most inferior aspect of the post 12. As flexion begins, the tibia is pulled posteriorly causing the femur to shift anteriorly with respect to the tibial platform. Such a shift may be enhanced where a heel strike occurs. As this anterior motion begins, the sliding surface of the cam 21 engages with the posterior surface 14 of the post 2112, thereby resisting anterior subluxation of the femur. While the flexion angle sweeps from 0 to 40 degrees, the sliding surface of the cam 21 remains in contact with the posterior surface 14 of the post 12 maintaining resistance to anterior subluxation of the femur.

Figure 7:
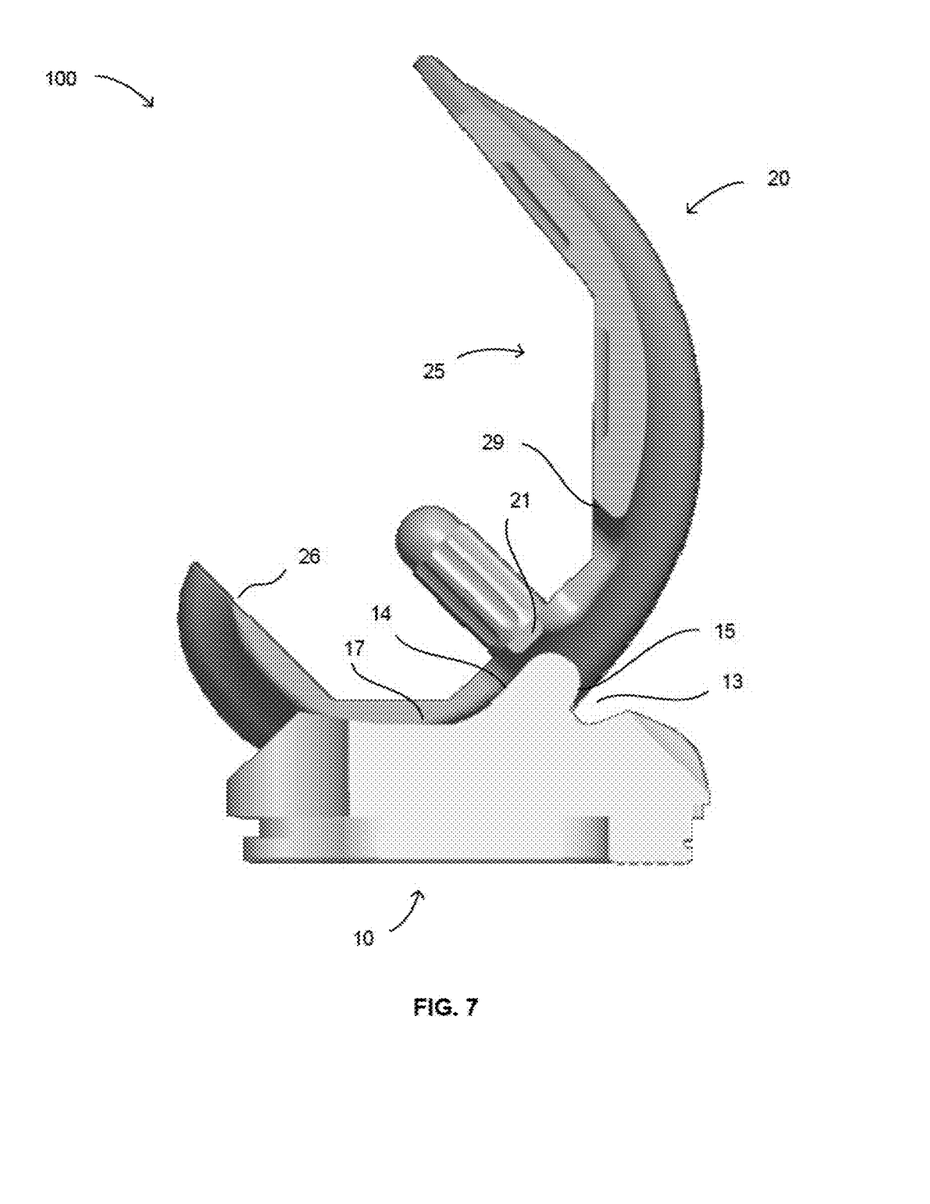
FIG. 7 shows a cross-sectional side view of the total knee prosthesis at 45 degrees of flexion.
Figure 8:
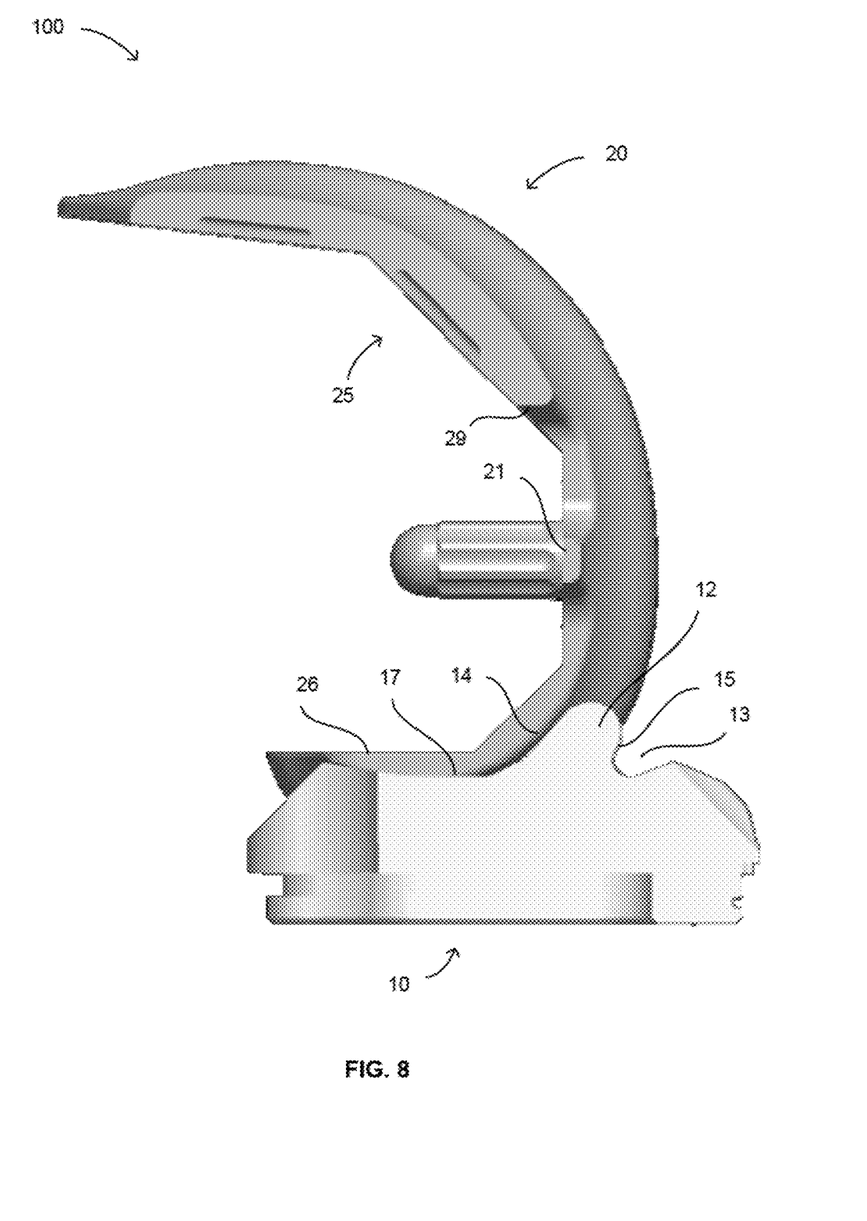
FIG. 8 shows a cross-sectional side view of the total knee prosthesis at 90 degrees of flexion.

Once flexion moves beyond 40 degrees, such as 45 degrees as shown in FIG. 7, the cam 21 moves superiorly to the post 12 resulting in disengagement with the post 12, at which point the cam no longer provides resistance to anterior translation, but the PCL is sufficiently tensioned to take control to prevent paradoxical movement. As flexion continues to 90 degrees of flexion as shown in FIG. 8, the cam 21 remains unengaged with the post 12 allowing for the natural PCL to restrain paradoxical movement and provide proprioception.

In order to provide for this anterior stabilization and proprioception, the post 12 is located far enough anteriorly on the tibial component 10 to prevent entanglement and interference with the PCL during articulation, and far enough posteriorly to ensure the cam 21 remains engaged with the post 12 through approximately 40 degrees of flexion. As best shown in FIGS. 2-3 and 5-8 and as previously mentioned herein, the post 12 is angled anteriorly with respect to the tibial component 10 and is curved in a sagittal plane. This angle allows for more natural articulation and for the post 12 to taper to a rounded edge to ensure the post 12 is guided into the engagement recess 23. Further, the angle of the post 12 and geometry of anterior surface 14 provides clearance space 13 for the femoral component 20 to ensure full extension of the knee joint, while prohibiting excessive hyperextension. Additionally, this space 13 allows the femoral component 20 to ride closely to the anterior surface 14 of the post to help prevent anterior subluxation of the tibia near full extension.

While the cam 21 may be cylindrical, it is preferably flattened to substantially match the planarity of the bone contacting surface 25. This allows for a more conforming fit with the resected femur. Further, it increases the surface area in contact with the post 12 to spread the contact forces out over a larger area in order to reduce wear and prevent slippage.

The advantages of this anterior cam 21 and post 12 mechanism is that it restricts anterior subluxation of the femur from 0 to 40 degrees of flexion to provide much needed anterior stabilization and enhanced proprioception, and also restricts anterior subluxation of the tibia through shallow angles of flexion. Further, the present invention does not interfere with natural knee mechanics once the PCL takes over beyond 40 degrees of flexion. Also, because the PCL is retained, natural kinematics such as roll-back are maintained. Thus, the more active patient is provided with a total knee prosthesis that suits their lifestyle.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A knee joint prosthesis, comprising:
a tibial component having concave articular surfaces and a post, first surface, and first recess each disposed between the concave articular surfaces, the first recess being located at a posterior aspect of the tibial component and being configured to receive a posterior cruciate ligament, the post extending from the first surface in a direction away from the first recess and having a second surface and a third surface disposed opposite the second surface, the first surface being adjacent to the second and third surfaces, the second and third surfaces each sloping away from the first recess toward an extent of the post; and
a femoral component having convex articular surfaces and a cam, second recess, and engagement recess each disposed between the convex articular surfaces, the cam being disposed between the second recess and engagement recess and having a sliding surface;
wherein the sliding surface slides along the first and second surfaces when the concave articular surfaces articulate with the convex articular surfaces.

2. The knee joint prosthesis of claim 1, wherein the cam slides along the first and second surfaces from 0 to 40 degrees of flexion of the knee joint.

3. The knee joint prosthesis of claim 2, wherein the second surface has a length such that the sliding surface lifts off of the second surface at about 40 degrees of flexion or more.

4. The knee joint prosthesis of claim 1, wherein the femoral component includes an abutment surface partially defining the second recess and is disposed opposite the cam, the abutment surface capable of contacting the third surface from about 0 to 20 degrees of flexion of the knee joint.

5. A prosthesis for replacing a knee joint, comprising:
a tibial component having concave articular surfaces and a post, superior surface, and recess each disposed between the concave articular surfaces, the post having a posterior surface and anterior surface each adjacent to the superior surface and each sloping upwardly from the superior surface in an anterior direction, the recess being configured to receive a posterior cruciate ligament; and
a femoral component having convex articular surfaces and a cam, second recess, and engagement opening each disposed between the convex articular surfaces, the cam being disposed between the second recess and engagement opening and having a sliding surface,
wherein the post extends at least partially through the engagement opening and the sliding surface slides along the posterior surface of the post during articulation of the knee joint.

6. The knee prosthesis of claim 5, wherein the posterior and anterior surfaces converge to at least partially define an extent of the post.

7. The knee prosthesis of claim 5, wherein the femoral component includes an abutment surface at least partially defining the opening, the abutment surface abuts the anterior surface of the post when a tibia shifts anteriorly with respect to a femur.

8. The prosthesis of claim 5, wherein:
the engagement opening extends through the femoral component and defines an abutment surface disposed opposite the cam, and
the anterior surface of the post has a length configured to permit abutment with the abutment surface throughout 0 to 20 degrees of flexion of the knee joint.

9. The prosthesis of claim 8, wherein:
the posterior surface has a length sufficient to permit contact with the cam throughout 0 to 40 degrees of flexion of the knee joint.

10. A knee prosthesis, comprising:
a tibial component having an articular surface, a posterior portion and an anterior portion, the posterior portion having a recess for receipt of a posterior cruciate ligament, the anterior portion having a post extending therefrom, the post having a posterior surface, anterior surface, and a superior extent, the posterior surface and anterior surface each sloping in an anterior direction from the anterior portion of the tibial component to the superior extent of the post; and
a femoral component having a condylar portion and an intercondylar portion, the intercondylar portion having a posterior recess for receipt of the posterior cruciate ligament, a cam, and an engagement recess for receipt of the post, the cam having a sliding surface and being disposed between the engagement recess and posterior recess, the engagement recess defining an abutment surface disposed opposite the cam,
wherein the sliding surface of the cam slides along the posterior surface of the post for restricting anterior subluxation of a femur bone when the articular surface and the condylar portion articulate through flexion of a knee joint, and wherein the abutment surface of the femoral component abuts the anterior surface of the post for restricting anterior subluxation of a tibia bone when the articular surface and condylar portion articulate through flexion of the knee joint.

11. The knee prosthesis of claim 10, wherein the sliding surface of the cam slides along the posterior surface of the post when the articular surface and the condylar portion articulate from 0 to 40 degrees of flexion of the knee joint.

12. The knee prosthesis of claim 11, wherein the sliding surface of the cam does not contact the posterior surface of the post when the articular surface and the condylar portion articulate beyond 40 degrees of flexion of the knee joint.

13. The knee prosthesis of claim 10, wherein the anterior surface at least partially defines a notch and faces toward a superior surface of the tibial component.

14. The prosthesis of claim 10, wherein when the articular surface and the condylar portion articulate through flexion of the knee joint, the cam is capable of sliding along the posterior surface of the post from about 0 to 40 degrees of flexion, and the abutment surface is capable of abutting the anterior surface of the post from about 0 to 20 degrees of flexion.

* * * * *